US009320541B2

(12) United States Patent
Smith (10) Patent No.: US 9,320,541 B2
(45) Date of Patent: Apr. 26, 2016

(54) TROCAR ASSEMBLY WITH OBTURATOR AND RETRACTABLE STYLET (75) Inventor: Robert C. Smith, Middletown, CT (US)

(73) Assignee: Covidien LP, Mansfield, MA (US)

(*) Notice: Subject to any disclaimer, the term of this patent is extended or adjusted under 35 U.S.C. 154(b) by 1604 days.

(21) Appl. No.: 12/526,091

(22) PCT Filed: Feb. 26, 2008

(86) PCT No.: PCT/US2008/002456
§ 371 (c)(1),
(2), (4) Date: Aug. 6, 2009

(87) PCT Pub. No.: WO2008/106085
PCT Pub. Date: Sep. 4, 2008

(65) Prior Publication Data
US 2010/0324488 A1 Dec. 23, 2010

Related U.S. Application Data (60) Provisional application No. 60/904,338, filed on Feb. 28, 2007.

(51) Int. Cl.
*A61B 17/34* (2006.01)
(52) U.S. Cl.
CPC .......... *A61B 17/3496* (2013.01); *A61B 17/3417* (2013.01); *A61B 2017/3454* (2013.01)
(58) Field of Classification Search
CPC .................... A61B 17/3417; A61B 2017/3454
See application file for complete search history.

(56) References Cited

U.S. PATENT DOCUMENTS

| 5,226,426 | A |   | 7/1993  | Yoon              |         |
|-----------|---|---|---------|-------------------|---------|
| 5,312,351 | A | * | 5/1994  | Gerrone           | 604/117 |
| 5,336,176 | A |   | 8/1994  | Yoon              |         |
| 5,474,539 | A | * | 12/1995 | Costa et al.      | 604/164.12 |
| 5,713,870 | A |   | 2/1998  | Yoon              |         |
| 5,772,678 | A |   | 6/1998  | Thomason et al.   |         |
| 6,063,099 | A | * | 5/2000  | Danks et al.      | 606/185 |
| 2001/0029387 | A1 | * | 10/2001 | Wolf et al.   | 606/184 |
| 2005/0107816 | A1 | * | 5/2005  | Pingleton et al. | 606/185 |
| 2011/0040149 | A1 | * | 2/2011  | Smith         | 600/114 |

FOREIGN PATENT DOCUMENTS

WO    WO 00/05679    9/2000

OTHER PUBLICATIONS

International Search Report for PCT/US2008/002456—date of mailing is Jul. 18, 2008 (1 page).
European Search Report from European Application No. EP 08 72 6041 mailed Nov. 30, 2012.

* cited by examiner

*Primary Examiner* — Aarti B Berdichevsky (57) ABSTRACT

A surgical system for penetrating tissue includes an obturator having an obturator housing and an obturator member extending from the obturator housing and having a penetrating member adapted to penetrate tissue. The penetrating member defines an outer wall with an irregular surface dimensioned to facilitate passage through tissue. The obturator may further include a stylet at least partially disposed within the obturator member. The stylet and the obturator member are adapted for relative longitudinal movement between a first relative position corresponding to an unarmed condition of the penetrating member and a second relative position corresponding to an armed condition of the penetrating member.

12 Claims, 12 Drawing Sheets

FIG. 26

TROCAR ASSEMBLY WITH OBTURATOR AND RETRACTABLE STYLET

CROSS REFERENCE TO RELATED APPLICATIONS

This application is a National Stage Application of PCT/US2008/002456 filed Feb. 26, 2008 under 35 USC 371 (a), which claims the benefit of and priority to U.S. Provisional Application Ser. No. 60/902,338 filed Feb. 28, 2007, the entire disclosure of which is incorporated herein by reference.

BACKGROUND

1. Technical Field

The present disclosure relates to a trocar assembly for use in minimally invasive surgical procedures, such as endoscopic or laparoscopic type procedures.

2. Background of the Related Art

Minimally invasive procedures are continually increasing in number and variation. Forming a relatively small diameter temporary pathway to the surgical site is a key feature of most minimally invasive surgical procedures. The most common method of providing such a pathway is by inserting a trocar assembly through the skin. In many procedures, the trocar assembly is inserted into an insufflated body cavity of a patient. In such procedures, the trocar assemblies with seal mechanisms are utilized to provide the necessary pathway to the surgical site while minimizing leakage of insufflation gases.

Trocar assemblies typically include an obturator which is removably inserted through a cannula. The obturator may include a safety shield which protects against unintentional puncturing by the sharpened tip of the obturator. The safety shield includes a mechanism which controls the relative movement and locking of the safety shield. One example of a safety shield mechanism is disclosed in commonly assigned U.S. Pat. No. 6,319,266 to Stellon et al., the entire contents of which are hereby incorporated by reference.

SUMMARY

Accordingly, the present disclosure is directed to further improvements in trocar technology. In one preferred embodiment, a surgical system for penetrating tissue includes an obturator having an obturator housing and an obturator member extending from the obturator housing and having a penetrating member adapted to penetrate tissue. The penetrating member defines an outer wall with an irregular surface dimensioned to facilitate passage through tissue. Preferably, the outer wall of the penetrating member includes a plurality of recesses therein. The recesses may extend in a general longitudinal direction and may be arranged in spaced selection. The outer wall of the penetrating end may define an undulating arrangement having a plurality of alternating raised portions and recessed portions.

In an alternate embodiment, the outer wall of the penetrating end includes a plurality of intersecting surfaces. The intersecting surfaces may be substantially planar. The penetrating end may define a polygonal cross-sectional dimension transverse to the longitudinal axis. In a further embodiment, the penetrating end defines a series of intersecting surfaces. The intersecting surfaces of adjacent series are arranged to intersect each other at an oblique angle. The intersecting surfaces may be substantially planar. Each of the series of the intersecting surfaces may define a polygonal cross-sectional dimension transverse to the longitudinal axis.

A preferred penetrating end includes a tapered section having the irregular surface and a cylindrical section extending from the tapered section to a penetrating tip.

The obturator may further include a stylet at least partially disposed within the obturator member. The stylet and the obturator member are adapted for relative longitudinal movement between a first relative position corresponding to an unarmed condition of the penetrating member and a second relative position corresponding to an armed condition of the penetrating member. The stylet may be adapted for longitudinal movement relative to the obturator housing between an extended position corresponding to the armed condition of the penetrating end of the obturator member and a retracted position corresponding to the unarmed condition of the obturator member. The stylet is preferably normally biased toward the extended position.

The surgical system may also include a cannula defining a longitudinal axis and having a longitudinal opening therethrough for at least partial reception of the obturator.

The obturator may include a latch member associated with the obturator housing. The latch member is moveable from an initial position securing the stylet in the extended position to a release position permitting the stylet to move to the retracted position. A release member may be mounted to the obturator housing and operatively coupled with the latch member. The release member is adapted to move the latch member to the release position during positioning of the obturator within the longitudinal opening of the cannula. The latch member may be monolithically formed with the obturator housing and arranged in cantilever relation therewith, and normally biased toward the initial portion thereof. The release member is adapted for movement relative to the obturator housing during positioning of the obturator within the longitudinal opening of the cannula, to thereby move the latch member to the release position. The release member preferably includes a release button dimensioned to extend distally beyond the obturator housing. The release button is positioned to engage a cannula housing of the cannula upon mating of the obturator housing and the cannula housing whereby a generally proximally directed force applied by the cannula housing on the release button causes displacement of the release member and movement of the latch member to the release position.

BRIEF DESCRIPTION OF THE DRAWINGS

Preferred embodiments of the present disclosure are described hereinbelow with references to the drawings, wherein.

DETAIL DESCRIPTION OF PREFERRED EMBODIMENTS

Figures 1, 2:
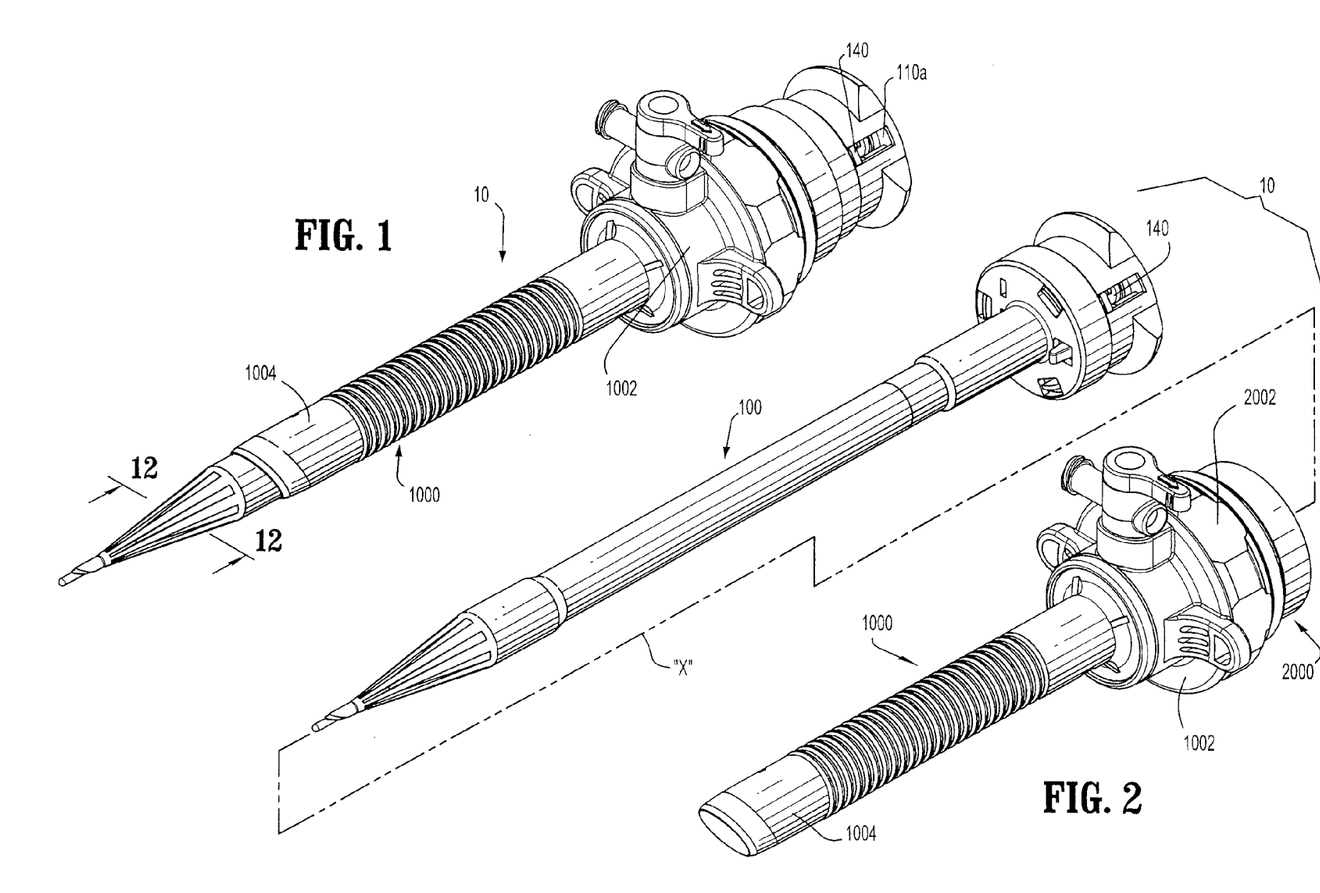
FIG. 1 is a perspective view of a trocar assembly in accordance with the principles of the present disclosure.
FIG. 2 is a perspective view with parts separated of the obturator assembly illustrating the cannula assembly and the obturator assembly.

Referring now in detail to the drawing figures, in which, like references numerals identify similar or identical elements, there is illustrated, in FIGS. 1 and 2, a trocar assembly constructed in accordance with a preferred embodiment of the present disclosure and designated generally by reference numeral 10. Trocar assembly 10 is particularly adapted for use in minimally invasive surgical procedures such as endoscopic or laparoscopic procedures. Generally, trocar assembly 10 includes two principal subassemblies, namely, obturator assembly 100 and cannula assembly 1000.

Cannula assembly 1000 may be any cannula assembly suitable for use in a laparoscopic surgical procedure. In one preferred embodiment, cannula assembly 1000 includes cannula housing 1002 and cannula sleeve 1004 extending from the cannula housing 1002. Either or both cannula housing 1002 and cannula sleeve 1004 may be transparent in part or in whole and may be fabricated from biocompatible metal or polymeric material. Cannula assembly 1000 may include an internal seal such as a duck-bill valve or other zero closure valve adapted to close in the absence of a surgical instrument to prevent passage of insufflation gases through the cannula assembly 1000.

Trocar assembly 10 may also include a seal assembly 2000 which is preferably releasably mounted to cannula housing 1002. Means for releasably connected seal assembly 2000 to cannula housing 1002 may include a bayonet coupling, threaded connection, latch, friction fit, tongue and groove arrangements, snap-fit, etc. Seal assembly 2000 includes seal housing 2002 and at least one internal seal which is adapted to form a fluid tight seal about an instrument inserted through the seal assembly 2000. One suitable seal may be the fabric seal disclosed in commonly assigned U.S. Pat. No. 6,702,787, which issued Mar. 9, 2004, the entire contents of which are incorporated herein by reference. The seal disclosed in the '630 patent may be a flat septum seal having a first layer of resilient material and a second fabric layer juxtaposed relative to the first layer. Further details of the seal may be ascertained by reference to the '787 patent. Seal assembly 2000 may or may not be a component of cannula assembly 1000. For example, the seal assembly may be a separate, removable assembly. In the alternative, the seal assembly may comprise an integral part of the cannula assembly 1000 and not be removable.

Figure 3:
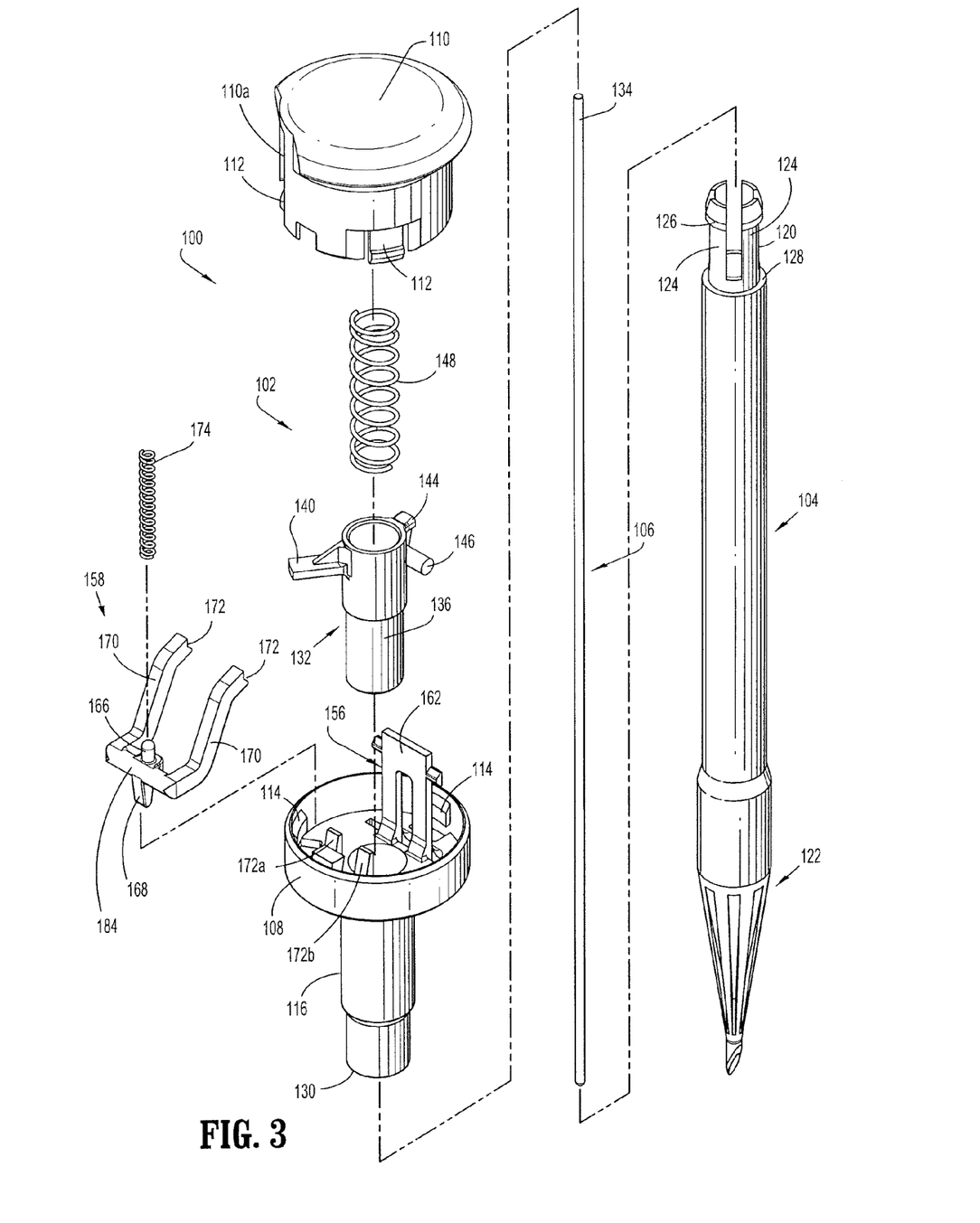
FIG. 3 is a perspective view with parts separated of the obturator assembly illustrating the obturator housing, the obturator member and the stylet.
Figures 4, 5:
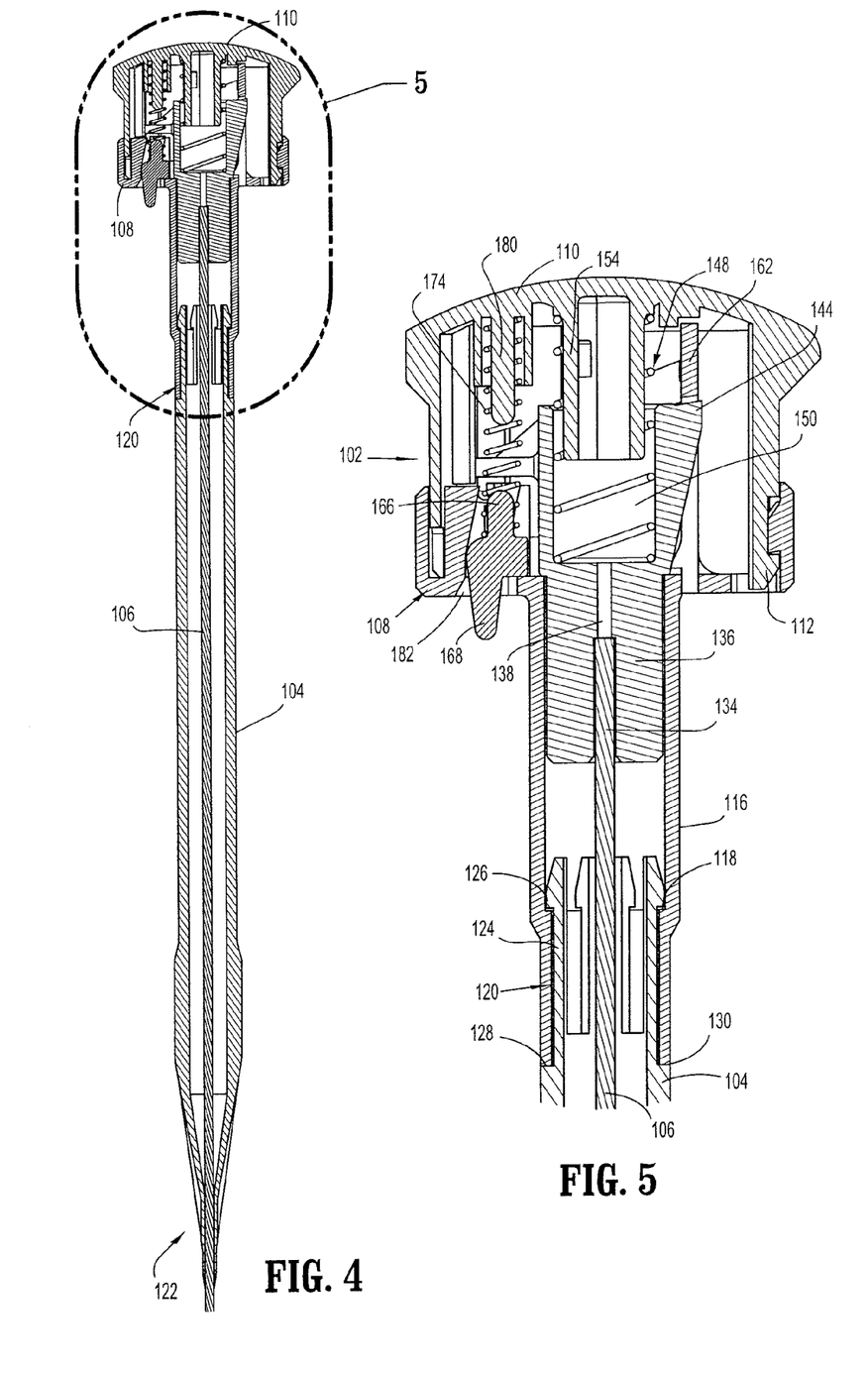
FIG. 4 is a side cross-sectional view of the obturator assembly.
FIG. 5 is an enlarged cross-sectional view of the indicated area of detail of FIG. 4.

With reference now to FIGS. 3-5, in conjunction with FIG. 2, obturator assembly 100 includes obturator housing 102, elongated obturator member 104 extending distally from the housing 102 and stylet 106 at least partially disposed within the obturator member 104. Obturator member 104 defines obturator axis "x" and will be discussed in greater detail hereinbelow. Obturator housing 102 includes housing base 108 and housing cover 110. Once the appropriate components are positioned therewithin (as described below), housing base 108 may be attached to housing cover 110 by engaging mating surfaces, for example, by resilient latches 112 of cover 110 interlocking with correspondingly dimensioned latch openings 114 of housing base 108. Preferably, to uniformly connect base 108 and cover 110 at least three corresponding latches 112 and openings 114 are spaced evenly around the circumference of the cover 110 and the base 108, respectively. Housing base 108 further defines base extension 116. Base extension 116 includes a stepped configuration defining an internal shelf 118 as best depicted in FIG. 5. Base extension 116 receives obturator member 104 to mount the obturator member 104 to the obturator housing 102.

With reference to FIGS. 3-5, obturator member 104 includes mounting extension 120 at its proximal end and penetrating end 122 at its distal end. Penetrating end 122 will be discussed in greater detail hereinbelow. Mounting extension 120 includes a plurality, e.g., four, of axially depending tabs 124. Tabs 124 define circumferential ledges 126. Tabs 124 are adapted to move radially inwardly upon initial insertion of mounting extension 120 within base extension 116 of obturator base 108, and thereafter return to their initial outward positions after circumferential ledges 126 clear internal shelf 118. In such position, circumferential ledges 126 of mounting extension 120 securely engage internal shelf 118 of housing base 108. Mounting extension 120 also defines outer annular shelf 128 which contacts the distal end 130 of base extension 116 thereby preventing movement of obturator member 104 in a proximal direction. Thus, the aforedescribed mounting arrangement of obturator member 104 and housing base 108 secures the obturator member 104 from moving in an axial direction relative to obturator housing 102. However, obturator housing 102 may rotate relative to obturator member 104. In particular, circumferential ledges 126 of obturator member 104 are dimensioned to slide along internal shelf 118 of base extension 106 during manipulation and use of the obturator assembly 100. Thus, during insertion, the operator may rotate obturator housing 102 without concern of underlying rotation of penetrating end 122 of obturator member 104.

Figure 6:
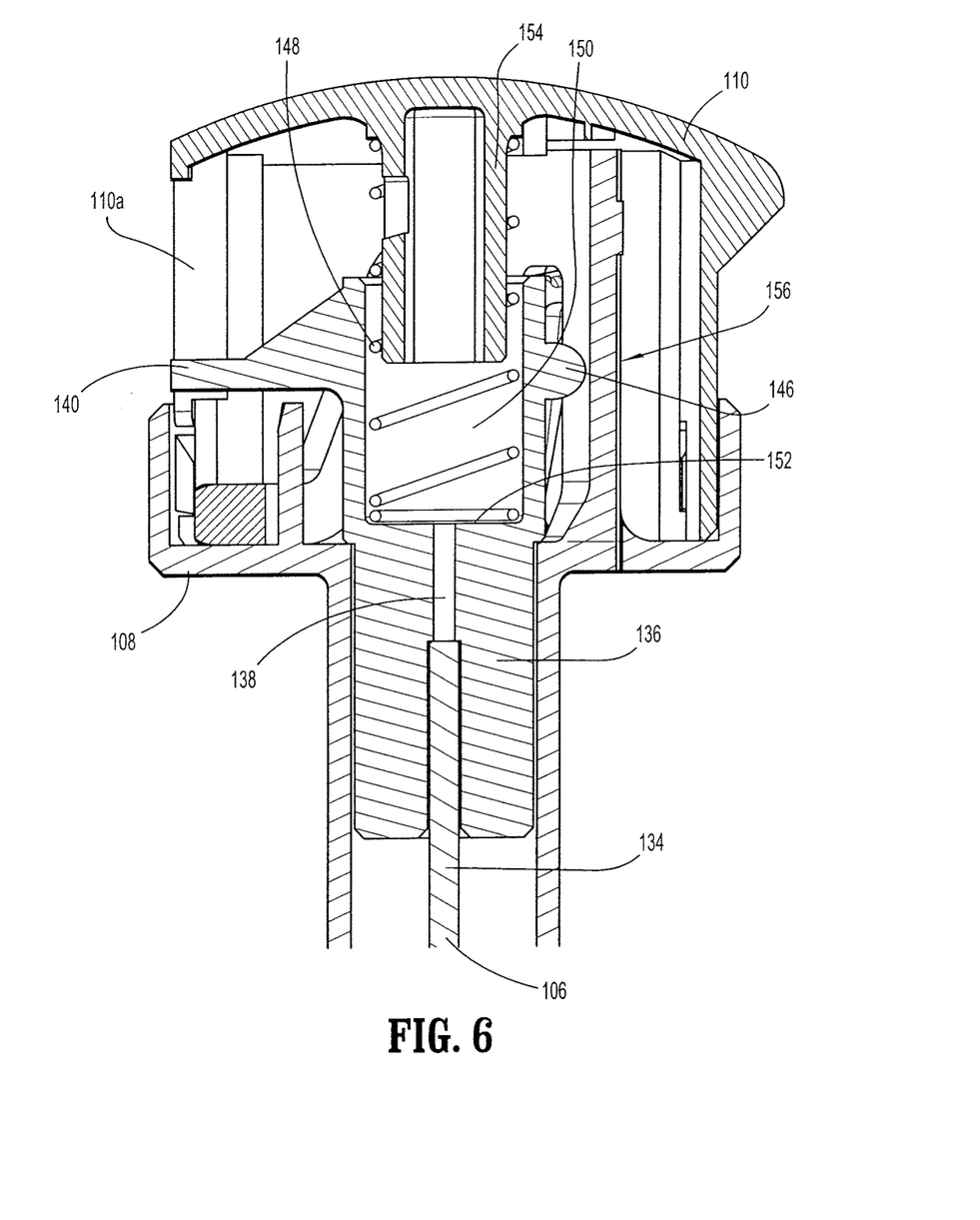
FIG. 6 is a second enlarged cross-sectional view of the obturator housing of the obturator assembly.
Figures 7, 8, 9:
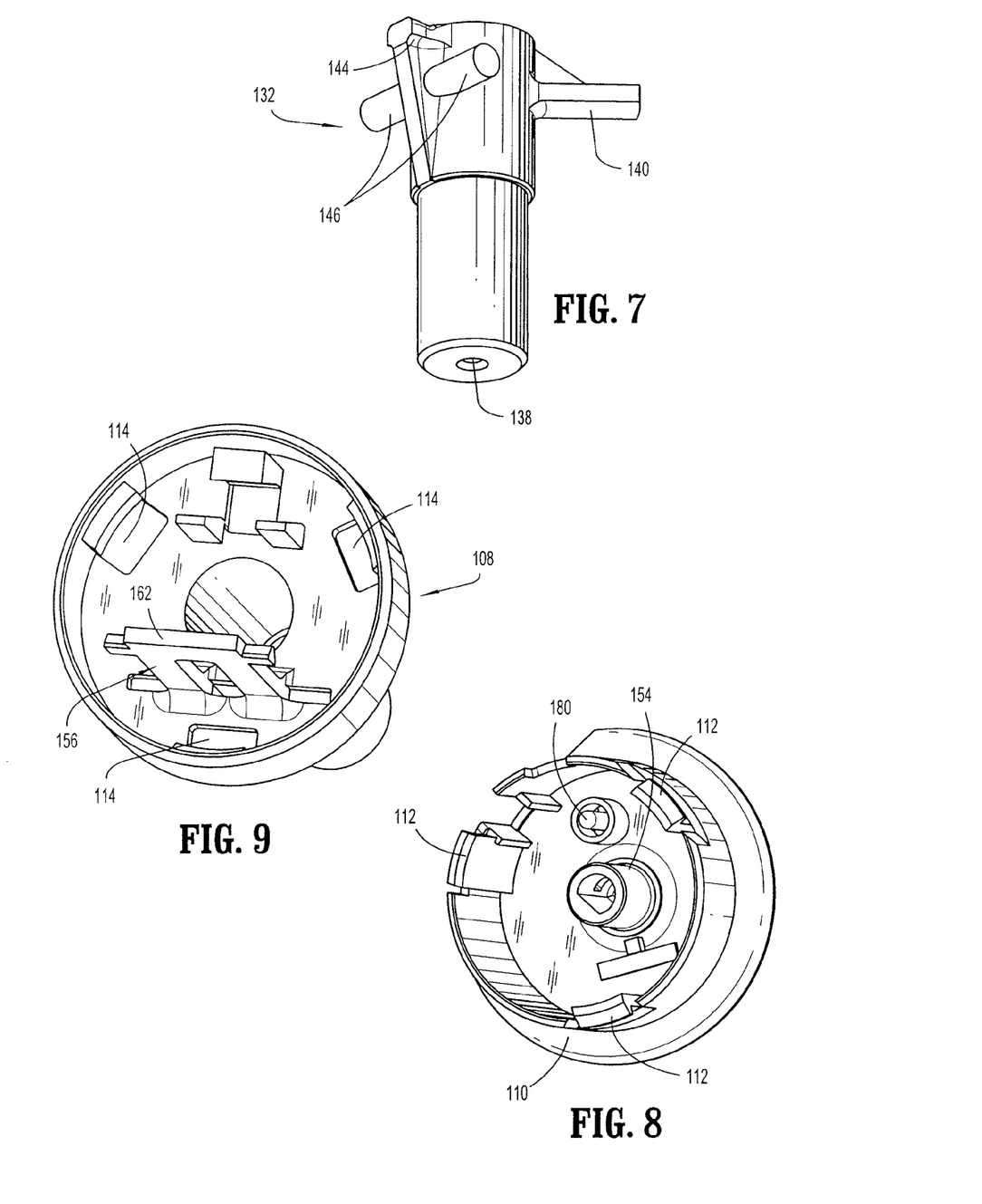
FIG. 7 is a perspective view of the indicator collar of the obturator housing.
FIG. 8 is a perspective view of the housing cover of the obturator housing.
FIG. 9 is a perspective view of the housing base of the obturator housing.

Referring now to FIGS. 5-7, in conjunction with FIG. 3, obturator assembly 100 further includes indicator collar 132 positioned within obturator housing 102 and secured to proximal end 134 of stylet 106. In one preferred arrangement, indicator collar 132 incorporates cylindrical section 136 defining internal bore 138 which receives proximal end 134 of stylet 106. Stylet 106 may be fixed within internal bore 138 through conventional means including cements, adhesives, interference fit, etc. With this arrangement, indicator collar 132 and stylet 106 move concurrently along the longitudinal axis "x" and relative to obturator housing 102 during use of the instrument.

Indicator collar 132 further includes a shield position indicator, such as indicator flag 140, extending transversely relative to the indicator collar 132. Indicator flag 140 is visible from the exterior of obturator housing 102 as it extends through groove 110a of housing cover 110 (see also FIGS. 2 and 6). Preferably, indicator flag 140 is colored to contrast sharply with the surrounding housing components. For example, indicator flag 140 may be red if the surrounding housing components are white or light colored. Indicator collar 132 further includes collar ledge 144 and a pair of posts 146 formed below the ledge 144 and extending radially outwardly from the ledge 144. Collar ledge 144 serves to releasably lock stylet 106 in a distal position corresponding to an unarmed condition of obturator assembly 100. FIG. 4 illustrates the unarmed condition of obturator assembly 100.

Indicator flag 140 and stylet 106 are spring biased in the distal direction by coil spring 148. In particular, coil spring 148 is received within internal bore 150 of indicator collar 132 and engages internal shelf 152 (see FIG. 6) of the indicator collar 132. The proximal end of coil spring 138 is coaxially mounted about spring mount 154 (see also FIG. 8) depending from the interior surface of housing cover 110.

Figure 10:
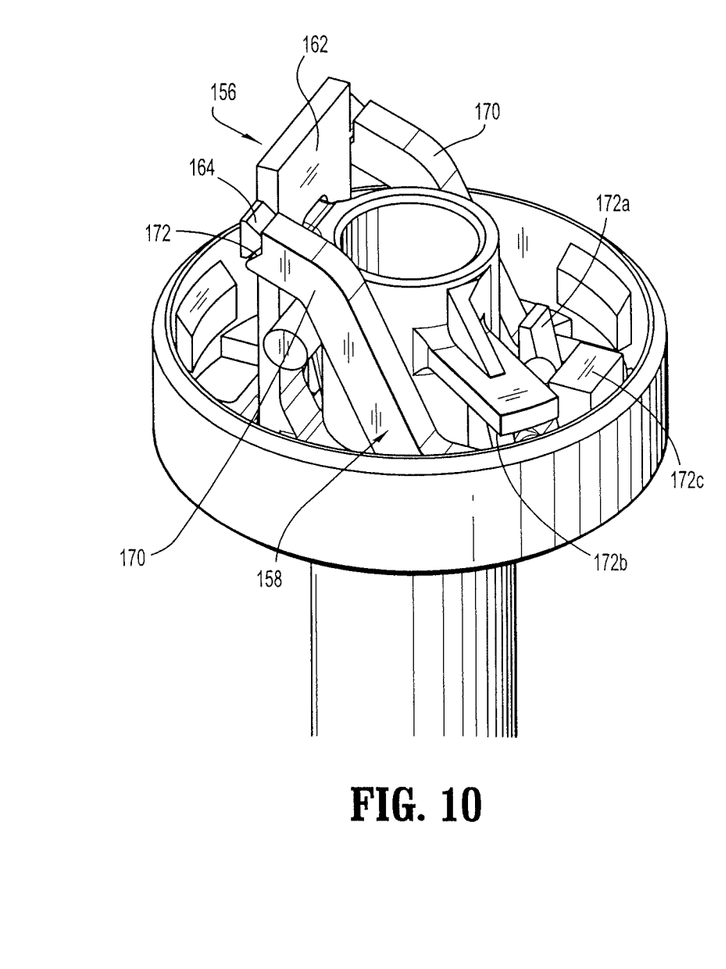
FIGS. 10-11 are perspective views illustrating the components of the latch mechanism.
Figure 11:
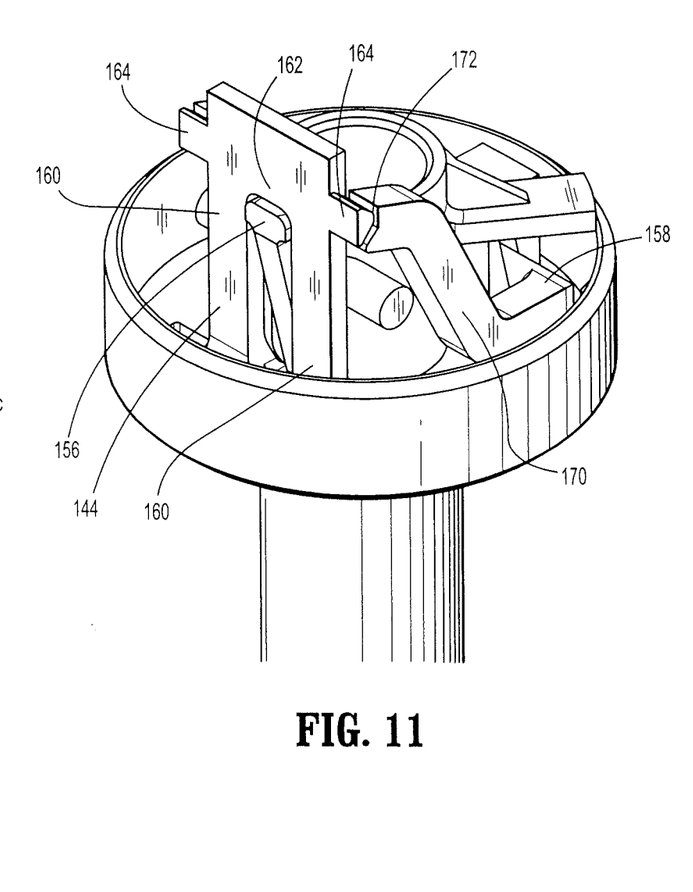

Referring now to FIGS. 9-11, in conjunction with FIGS. 3-5, obturator assembly 100 includes a latching mechanism disposed within obturator housing 102 to prevent proximal movement of stylet 106 until such time as the obturator assembly 100 is mounted to cannula assembly 1000 and the surgeon is prepared to begin trocar entry. Latching mechanism includes latch member 156, and release member such as slider 158, as best seen in FIG. 3. Latch member 156 has two vertical legs 160 connected by web 162. A pair of biasing posts 164 extends outwardly, one for each side of latch member 156. Collar ledge 144 of indicator collar 132 is engaged and secured by web 162 of latch member 156 when in an initial position of the latch member 156 as depicted in FIGS. 10-11. In the initial position of latch member 156, stylet 106 is retained in a first extended position shown in FIG. 4 corresponding to the unarmed condition of obturator assembly 100. Latch member 156 is preferably molded as part of housing base 106 in cantilever fashion. However, latch member 156 may be formed as a separate element and secured to base 106 by suitable known techniques.

Slider 158 includes post 166 disposed at its lower end, arming button 168 extending distally from the distal face of slider 158 and a pair of slider legs 170 which terminate in crooks 172. Crooks 172 defined in slider legs 170 are configured and dimensioned to engage posts 164 of latch member 156, as shown in FIGS. 10 and 11. Slider 158 is distally biased by slider spring 174 which is maintained in axial alignment by slider post 166 of slider 158. The proximal end of slider spring 174 bears against the inner surface of housing cover 110 and is maintained in position between proximal post 178 and cylindrical post 180 formed in the housing cover 110 (see FIG. 5). The distal biasing of slider 158 causes arming button 168 to project through opening 182 formed in housing base 106. The lower end or transverse leg 184 of slider 158 resides with mounting posts 172a-c of housing base 106 with post base 184 of slider 158 residing within mounting posts 172b, 172c. (See FIG. 10). Mounting of obturator assembly 100 relative to cannula assembly 112 causes slider 158 to translate or rotate generally vertically in a generally proximal direction as will be described further hereinbelow.

Figure 12:
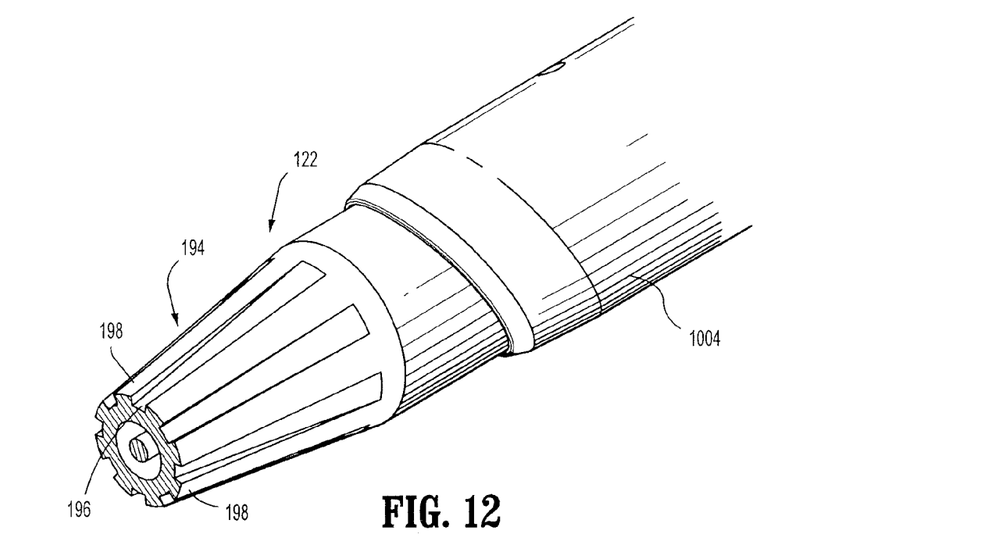
FIG. 12 is a perspective view in partial cross-section taken along the lines 12-12 of FIG. 1 illustrating the obturator member and the stylet.
Figure 13:
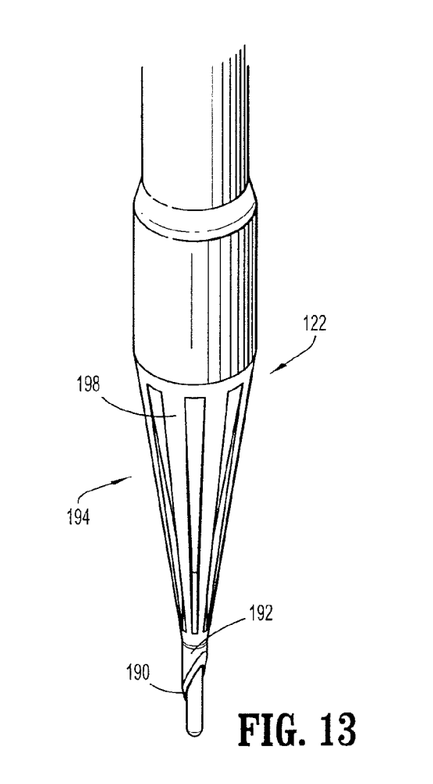
FIGS. 13-14 are perspective views illustrating the stylet in respective advanced and retracted positions relative to the obturator member.
Figure 14:
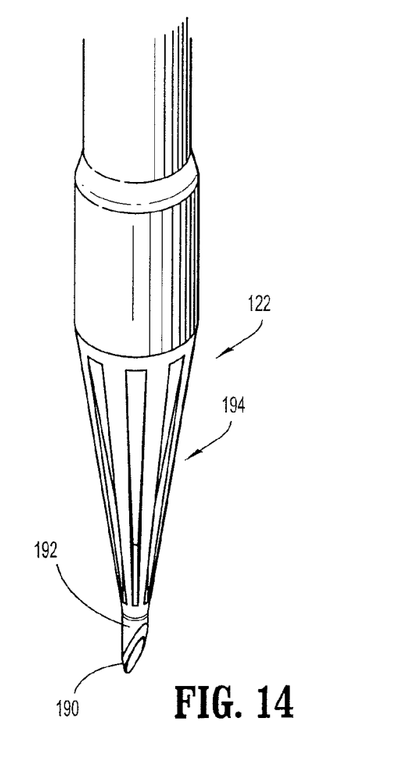

With reference to FIGS. 12-14, penetrating end 122 of obturator member 104 will be discussed. Penetrating end 122 of obturator member 104 generally tapers inwardly relative to longitudinal axis "x" towards penetrating tip 190. Penetrating tip 190 defines a general beveled arrangement, and may have a sharpened edge or may be generally blunt if desired. Extending contiguously from penetrating tip 190 is an annular, e.g., cylindrical, end portion 192 of relatively small diameter. Cylindrical end portion 192 provides a reduced profile when viewed axially to facilitate initial passage of penetrating end 122 through tissue. Tapered section 194 extends contiguously from cylindrical end portion 192. In a preferred embodiment, tapered section 194 includes a plurality of recesses 196 which extend in a longitudinal direction. Recesses 196 are preferably radially spaced to define an alternating arrangement of outward, e.g., convex portions 198, and inward, e.g., concave portions or recesses 196. Recesses 196 are dimensioned to receive tissue displaced during insertion of obturator member 104 to facilitate passage of penetrating end 122 through tissue. Outward portions and inward portions 198, 196, e.g., may be rectilinear as shown, or in the alternative may have an arcuate character.

Stylet 106 may be any suitable relatively rigid member and preferably defines a rounded or blunted end to minimize trauma to tissue.

Figures 15, 16:
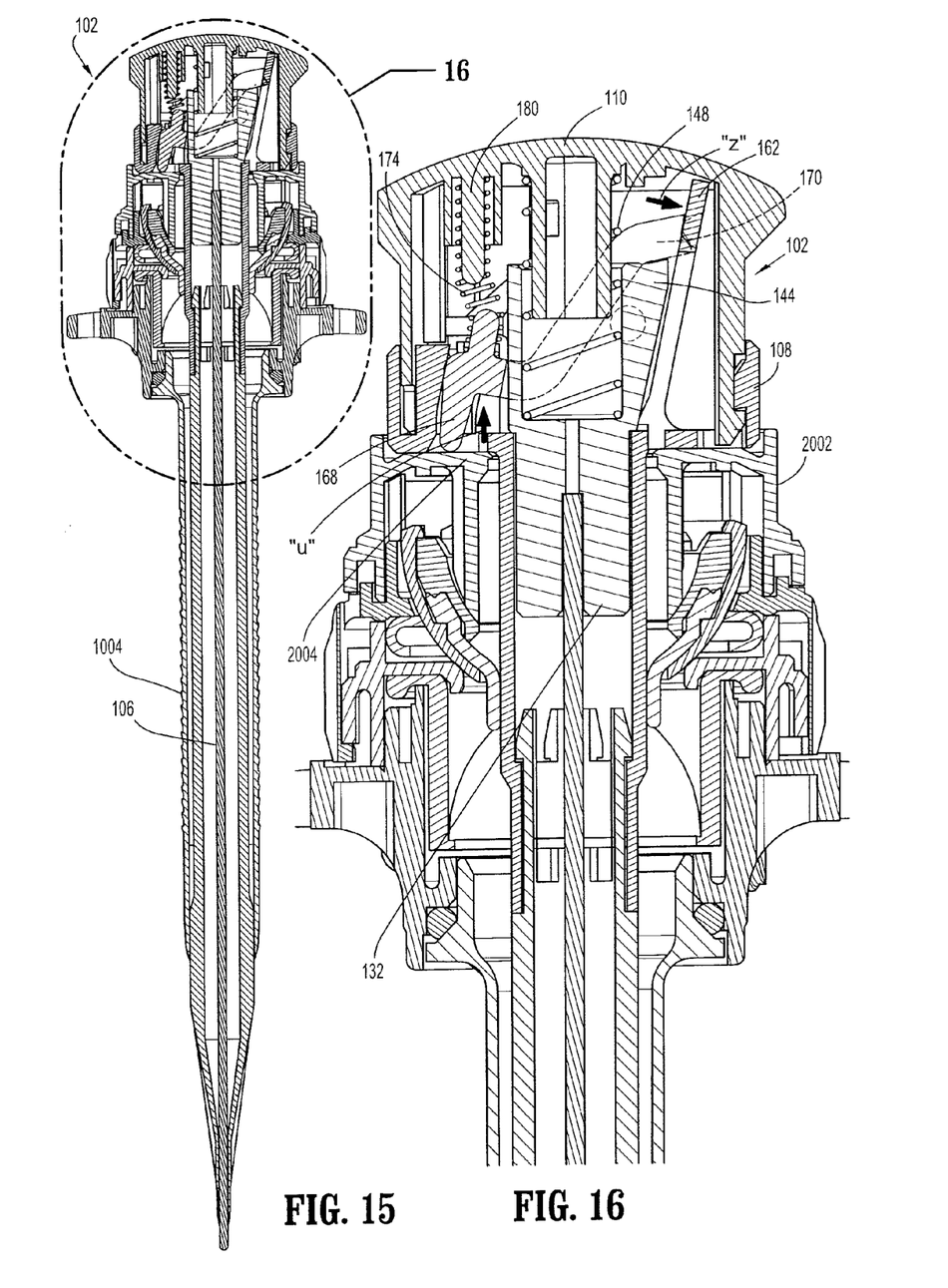
FIG. 15 is a side cross-sectional view of the trocar assembly illustrating the obturator assembly mounted relative to the cannula assembly and the latch member in an actuated position.
FIG. 16 is a view of the indicated area of detail of FIG. 15 illustrating the relationship of the components of the latch member in the actuated position.

With reference now to FIGS. 15-16, a method of use and operation of trocar assembly 10 will be discussed. Obturator assembly 100 is inserted within cannula assembly 1000 and advanced to where obturator housing 102 is approximated with seal housing 2002 of the seal assembly 2000. Seal assembly 2000 may comprise a separate part or may be a component of cannula assembly 1000. Seal housing 2002 and housing base 108 of obturator housing 102 may be appropriately dimensioned to form a friction fit or may be coupled to each other by conventional means including bayonet coupling, tongue-groove, etc. Approximating the obturator housing 102 and the seal housing 202 releases the stylet 106 from a locked condition, actuating the trocar assembly. With the obturator housing 102 and seal housing 2002 approximated, arming button 168 of slider 158 engages surface 2004 of seal housing 2002 and is forced upwardly (depicted by directional arrow "u") from the position depicted in FIG. 5 to the position depicted in FIGS. 15-16. During this movement, slider 158 pivots or angulates whereby legs 170 of slider 158 push latch member 156 in a radial outward direction (depicted by directional arrow "z") such that web portion 162 of latch member 156 is out of axial alignment with ledge 144 of indicator collar 132. In this position, indicator collar 132 and stylet 106 are free to axially move.

Figures 17, 18:
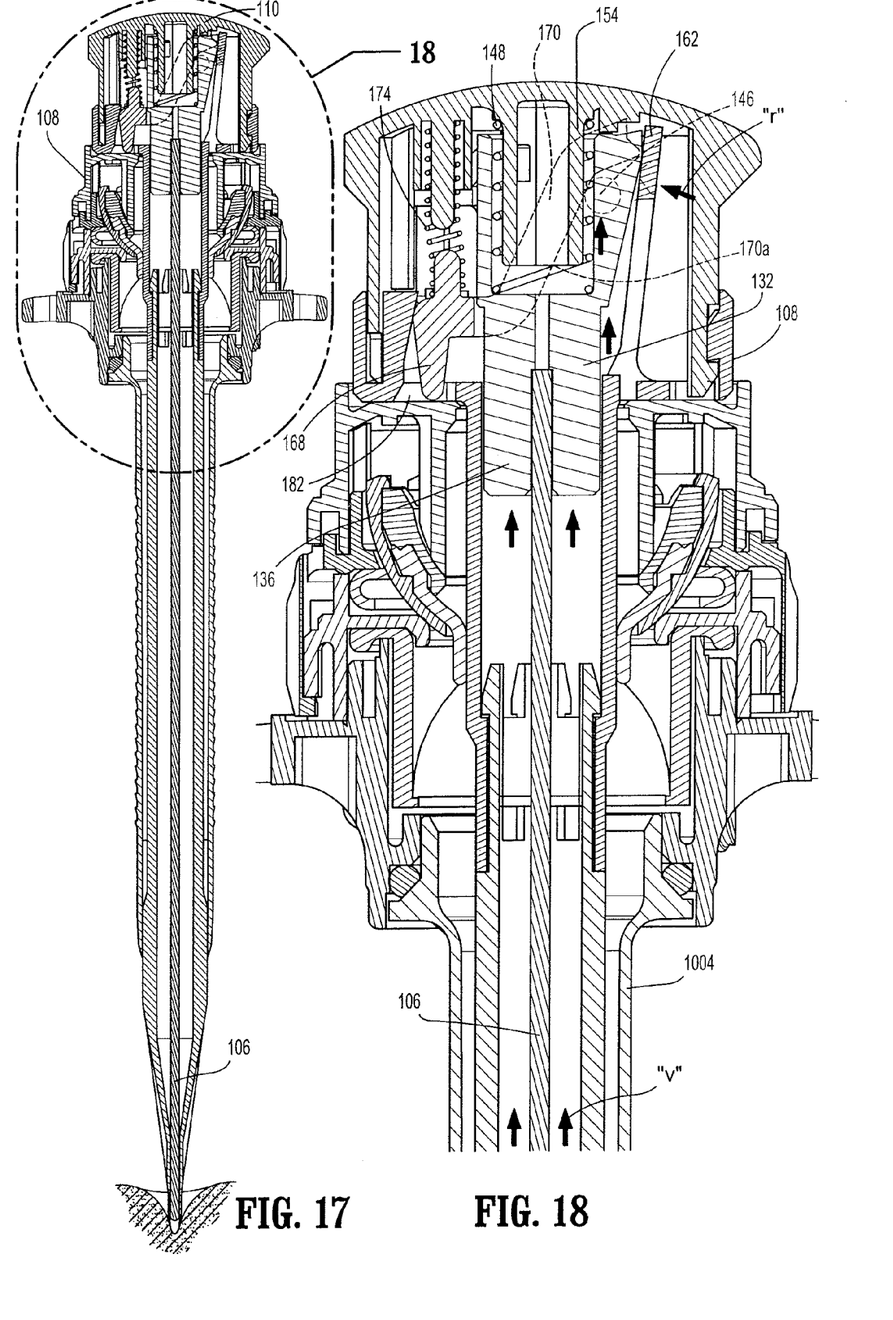
FIG. 17 is a view similar to the view of FIG. 15 illustrating the stylet of the obturator assembly in a retracted position.
FIG. 18 is a view of the indicated area of detail of FIG. 17 illustrating the relationship of the components of the latch member when the stylet is in the retracted position.
Figure 19:
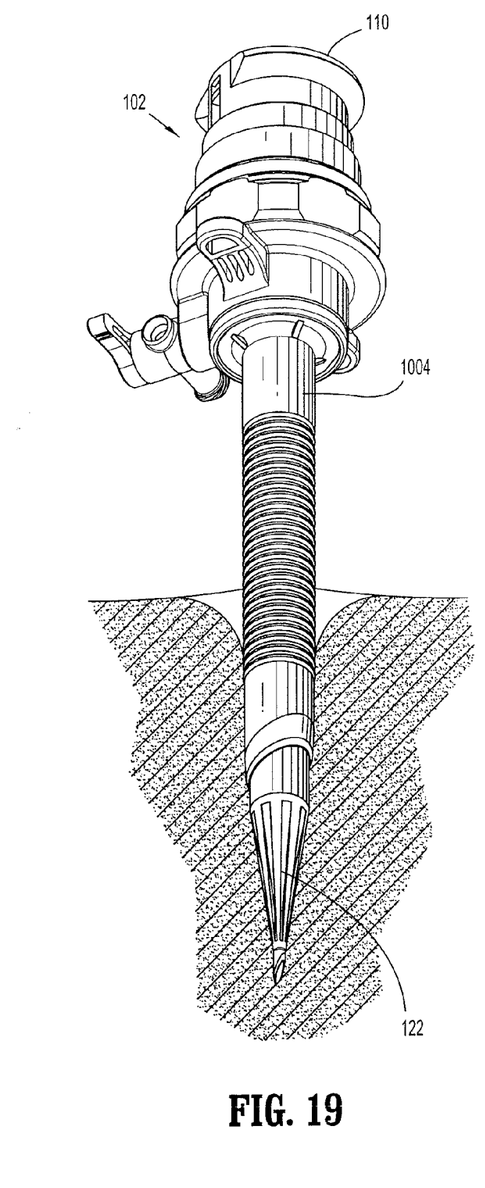
FIG. 19 is a perspective view illustrating insertion of the trocar assembly within tissue.
Figure 20:
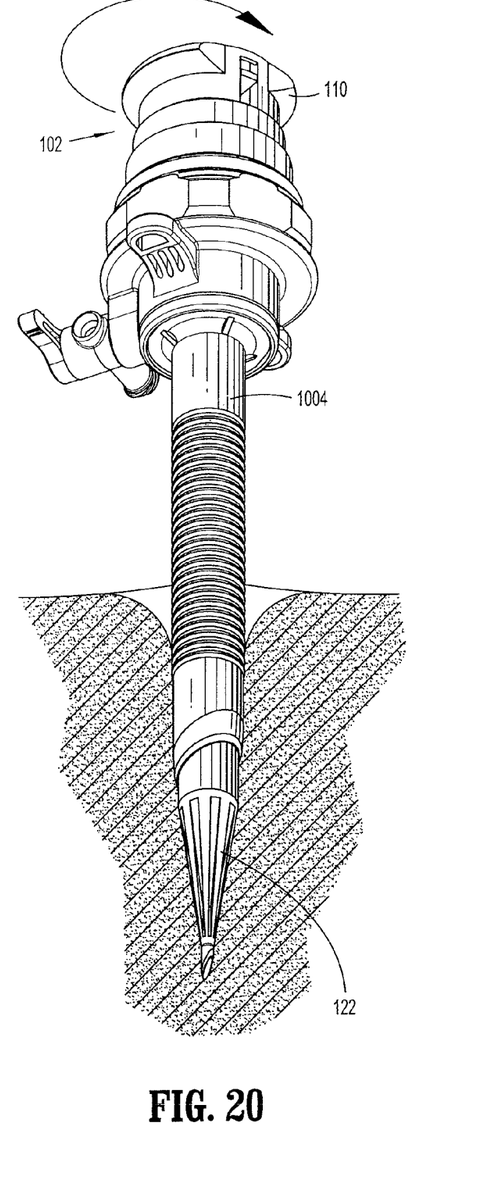
FIG. 20 is a view similar to the view of FIG. 19 illustrating rotation of the obturator housing of the obturator assembly.

Referring now to FIGS. 17-18, the surgeon begins to insert trocar assembly 10 through the body wall of the patient. Stylet 106 contacts the tissue and is driven upwardly to cause the stylet 106 and indicator collar 132 to move proximally (depicted by directional arrow "v") against the bias of coil spring 148. Such movement exposes the penetrating tip 190 of penetrating end 122 of obturator member 104 to incise the tissue as shown in FIG. 17. This armed condition of obturator assembly 100 is visually verified by the proximal location of indicator flag 140 of indicator collar 132. In addition, proximal movement of indicator collar 132 causes posts 146 of the indicator collar 132 to ride along outer surfaces 170a of legs 170 of slider 158 to thereby move the slider 158 at least radially inwardly and upwardly (as shown by the directional arrows "r") in a general aligned position relative to the obturator axis "x". FIG. 18 illustrates this actuated position of latch member 156. With penetrating tip 190 exposed, the surgeon may apply a distally-directed force to obturator assembly 100 to cause penetration through the tissue. The surgeon may rotate obturator housing 102 during manipulation and advancement of obturator assembly 100 into the tissue without concern of corresponding rotation of penetrating end 122. FIGS. 19-20 illustrate rotation of obturator housing 102 while penetrating end 122 remains stationary during advancement of trocar assembly 10 within tissue "t". It is noted that indicator flag 140 in its proximal position provides visual confirmation of the armed condition of knife blade 190.

Once penetrating tip 190 and stylet 106 pass through the body wall of the patient, the stylet 106 moves distally to extend beyond penetrating tip 190 to assume the unarmed condition depicted in FIG. 4. In particular, indicator collar 132 and stylet 106 are driven distally under the influence of coil spring 148. Concurrently with this movement, slider 158, which is aligned relative to axis "x", is driven distally under the influence of coil spring 174. In the respective positions of indicator collar 132 and slider 158 depicted in FIGS. 4 and 5, collar ledge 144 of indicator collar 132 securely engages web 162 of latch member 156 to secure stylet 106 in the extended position. The obturator assembly 100 is removed from cannula assembly 1000 and surgery is performed with instruments inserted through cannula assembly 1000.

Figures 21, 22, 23:
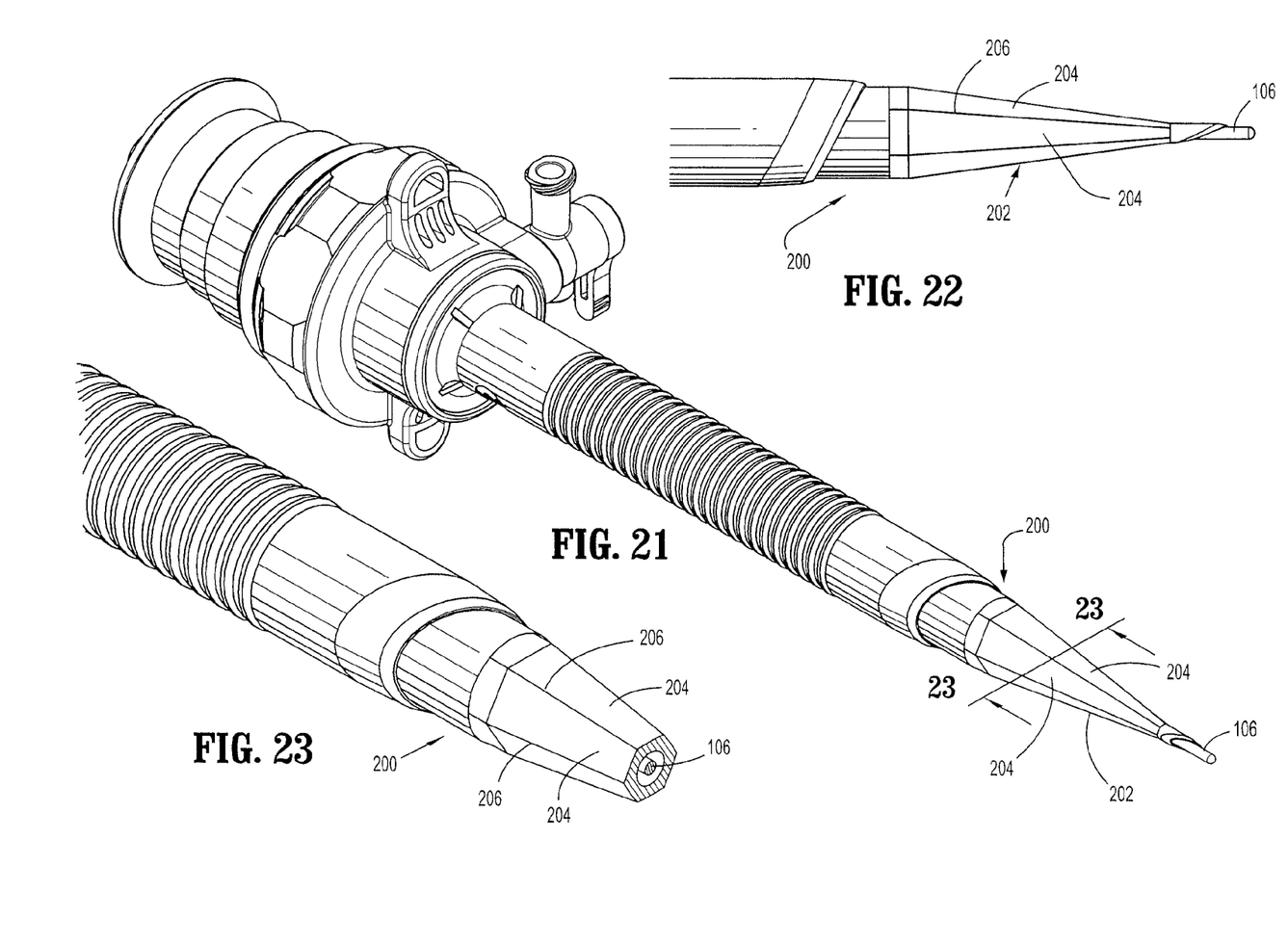
FIG. 21 is a perspective view of the trocar assembly incorporating an alternate embodiment of the obturator member.
FIG. 22 is a side plan view illustrating the distal end of the obturator member of FIG. 21.
FIG. 23 is a perspective view in partial cross-section taken along the lines 23-23 of FIG. 21.

With reference to FIGS. 21-23, an alternative embodiment of penetrating end 200 of obturator member 104 is illustrated. In accordance with the embodiment, tapered section 202 of penetrating end 200 includes a plurality of intersecting surfaces 204. Surfaces 204 may be substantially planar as shown or may have an arcuate characteristic including concave or convex arrangements. In one preferred embodiment, tapered section 202 defines a polygonal cross-sectional dimension transverse to the longitudinal axis, and more preferably, a hexagonal configuration with six substantially planar intersecting surfaces 204. As appreciated, tapered section 202 may include three or more surfaces, and is not limited to six intersecting surfaces 204. The lines of intersection 206 of adjacent intersecting sides 204 may be generally sharp to incise tissue, or, in the alternative, may be blunt.

Figures 24, 25, 26:
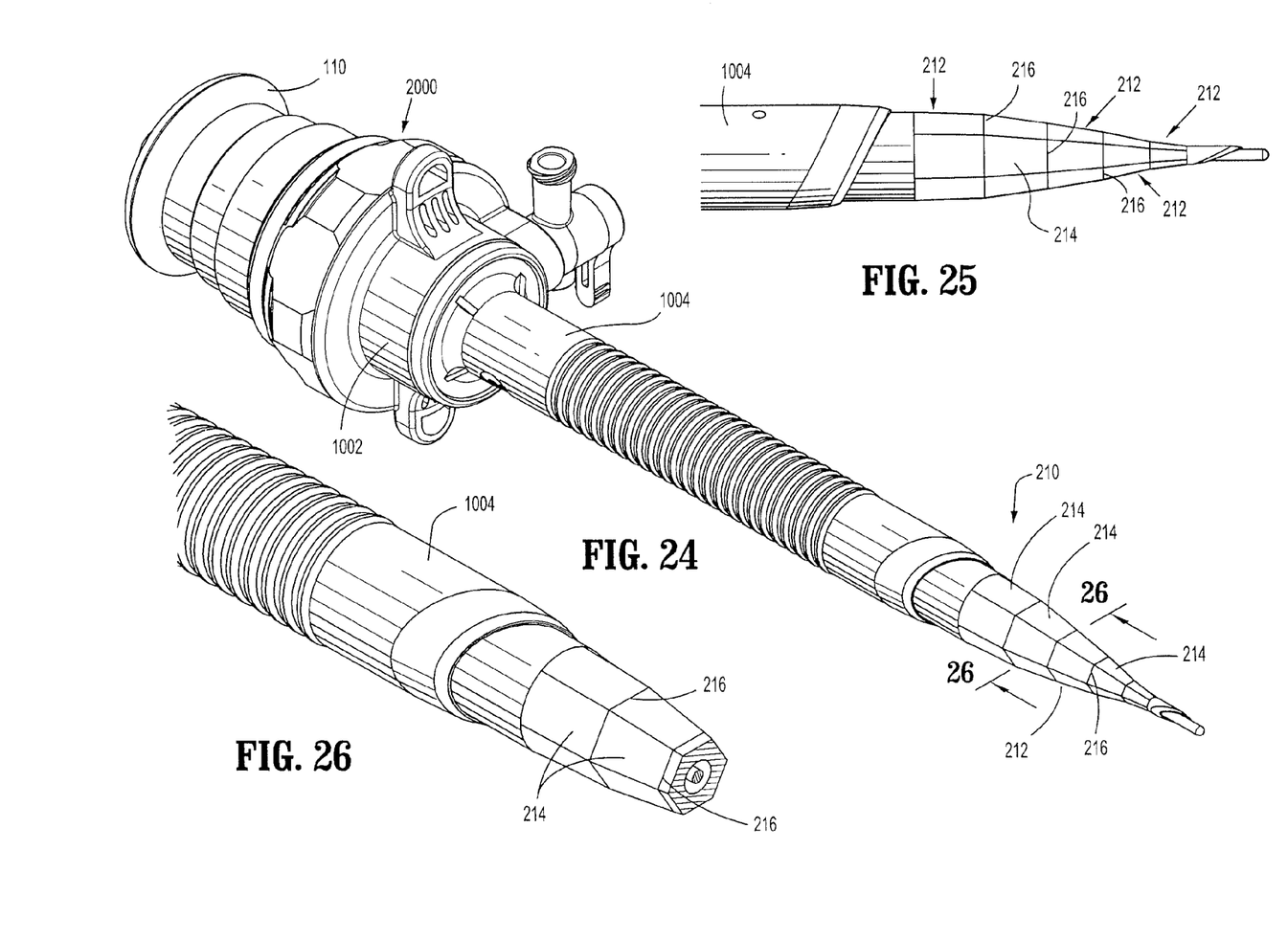
FIG. 24 is a perspective view of the trocar assembly incorporating another alternative embodiment of the obturator member.
FIG. 25 is a side plan view illustrating the distal end of the obturator member of FIG. 24.
FIG. 26 is a perspective view in partial cross-section taken along the lines 26-26 of FIG. 24.

FIGS. 24-26 illustrate another embodiment of the penetrating end 210 of obturator member 104. Penetrating end 210 includes a series 212 of intersecting surfaces 214. Each series 212 is arranged in oblique relation with an adjacent series 212 thereby creating transverse lines of intersection 216 between the longitudinally arranged series 212. The number of intersecting surfaces 214 within each series 212 may be six or more or less than six. Surfaces 214 may be substantially planar, convex or concave. Transverse lines of intersection 216 between the series 212 and longitudinal lines of intersection between intersecting surfaces 214 within the series may be sharpened or blunt. If sharp, the transverse lines of intersection provide a substantial incising capability to penetrating end 210.

The materials utilized in the components of the presently disclosed trocar assembly generally include materials such as, for example, ABS, polycarbonate, stainless steel, titanium and any other suitable biocompatible metals and/or polymeric materials. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that the penetrating end may have different configurations such as the tapered or conical configuration disclosed in commonly assigned U.S. provisional application Ser. No. 60/875,147, filed on Dec. 15, 2006, the entire contents of which are hereby incorporated by reference. Other configurations are also envisioned.

What is claimed is:

1. A surgical system for penetrating tissue, which comprises:
an obturator including an obturator housing and an obturator member extending from the obturator housing and defining a longitudinal axis, the obturator member having a penetrating member dimensioned and adapted to penetrate tissue, the penetrating member defining a substantially continuous annular outer wall having a plurality of longitudinal recessed surface portions, the longitudinal recessed portions extending toward a beveled penetrating tip and being in oblique relation to the longitudinal axis, adjacent recesses being in radial spaced relation, the recessed portions dimensioned to receive tissue displaced during advancement of the penetrating member to facilitate passage through tissue; wherein the penetrating member includes a tapered section having the plurality of longitudinal recessed surface portions, and a cylindrical section extending from the tapered section to the beveled penetrating tip.

2. The surgical system according to claim 1 wherein the outer wall of the penetrating member defines an undulating arrangement having a plurality of alternating raised portions and recessed portions when viewed in cross-section orthogonal to the longitudinal axis.

3. The surgical system according to claim 1 wherein the penetrating member is monolithically formed.

4. A surgical system for penetrating tissue, which comprises:
an obturator including an obturator housing and an obturator member extending from the obturator housing and defining a longitudinal axis, the obturator member having a penetrating member dimensioned and adapted to penetrate tissue, the penetrating member defining a substantially continuous annular outer wall having a plurality of longitudinal recessed surface portions, the longitudinal recessed portions extending toward a penetrating tip and being in oblique relation to the longitudinal axis, adjacent recesses being in radial spaced relation, the recessed portions dimensioned to receive tissue displaced during advancement of the penetrating member to facilitate passage through tissue; and
a stylet at least partially disposed within the obturator member, the stylet and the obturator member being adapted for relative longitudinal movement between a first relative position corresponding to an unarmed condition of the penetrating member and a second relative position corresponding to an armed condition of the penetrating member.

5. The surgical system according to claim 4 wherein the stylet is adapted for longitudinal movement relative to the obturator housing between an extended position corresponding to the armed condition of the penetrating member of the obturator member and a retracted position corresponding to the unarmed condition of the obturator member.

6. The surgical system according to claim 5 wherein the stylet is normally biased toward the extended position.

7. The surgical system according to claim 6 including a cannula defining a longitudinal axis and having a longitudinal opening therethrough for at least partial reception of the obturator.

8. The surgical system according to claim 7 including a latch member associated with the obturator housing, the latch member being moveable from an initial position securing the stylet in the extended position to a release position permitting the stylet to move to the retracted position.

9. The surgical system according to claim 8 including a release member mounted to the obturator housing and operatively coupled with the latch member, the release member adapted to move the latch member to the release position during positioning of the obturator within the longitudinal opening of the cannula.

10. The surgical system according to claim 9 wherein the latch member is monolithically formed with the obturator housing and arranged in cantilever relation therewith and being normally biased toward the initial portion thereof.

11. The surgical system according to claim 9 wherein the release member is adapted for movement relative to the obturator housing during positioning of the obturator within the longitudinal opening of the cannula, to thereby move the latch member to the release position.

12. The surgical system according to claim 11 wherein the release member includes a release button, the release button dimensioned to extend distally beyond the obturator housing, and positioned to engage a cannula housing of the cannula upon mating of the obturator housing and the cannula housing whereby a generally proximally directed force applied by the cannula housing on the release button causes displacement of the release member and movement of the latch member to the release position.

* * * * *